US006403081B1

(12) United States Patent
Papadopoulou et al.

(10) Patent No.: US 6,403,081 B1
(45) Date of Patent: Jun. 11, 2002

(54) ATTENUATED STRAINS OF LEISHMANIA AND USES THEREOF

(75) Inventors: Barbara Papadopoulou; Marc Ouellette; Martin Olivier, all of Quebec (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

(21) Appl. No.: 09/617,852

(22) Filed: Jul. 17, 2000

Related U.S. Application Data

(62) Division of application No. 08/643,751, filed on May 6, 1996, now Pat. No. 6,162,638.

(51) Int. Cl.$^7$ .................. A01N 63/00; A01N 65/00; A61K 48/00; A61K 39/00; A61K 39/002
(52) U.S. Cl. .................. 424/93.1; 424/93.2; 424/93.21; 424/184.1; 424/265.1; 424/269.1
(58) Field of Search .................. 424/93.1, 93.2, 424/93.21, 184.1, 265.1, 269.1

(56) References Cited

FOREIGN PATENT DOCUMENTS

WO    WO 95/06729    3/1995

OTHER PUBLICATIONS

Beverly et al (Annals of Tropical Med & Parasitology vol. 89 Supp 1 pp 11–17), 1995.*

Khalil et al (Lancet vol. 356 pp 1565–1569), Nov. 4, 2000.*

WHO, Tropical Disease Report, 1989. pp. 85–92.

Turco, S.J. and Descoteaux, A., 1992. The lipophosphoglycan of Leishmania parasites. Annu. Rev. Microbiol. 46:65–94.

Modabber, F. 1989. Experiences with vaccines against cutaneous leshmaniasis: of men and mice. Parasitol. 98:S49–S60.

Fairlamb, A.H., Blackburn, P., Ulrich, P., Chait, B.T and Cerami, A. (1985) Trypanothione: a novel bis(glutathionyl) spermidine cofactor for glutathione reductase in trypanosomatids. Science 227:1485–1487.

Schirmer, R.H., and Schulz, G.E. (1987) in: Pyridine Nucleotide Coenzymes, Part B. Coenzymes and Cofactors, vol. 2, Wiley, New York, pp. 333–379.

Shames, S.L., Fairlamb, A.H., Cerami, A., and Walsh, C.T. (1986) Purification and characterization of trypanothione reductase from *Crithidia fasciculata*, a newly discovered member of family of disulphide–containing flavoprotein reductases. Biochemistry 25: 3519–3526.

Fairlamb, A.H., and Cerami, A. (1992). Metabolism and functions of trypanothione in the Kinetoplastida. Annu. Rev. Microbiol. 46:695–729.

Krauth–Siegel, R.L., Enders, B., Henderson, G.B., Fairlamb, A.H., and Schirmer, R.H. (1987). Trypanothione reductase from *Trypanosome cruzi*: purification and characterization of the crystalline enzyme. Eur. J. Biochem. 164:123–128.

Taylor, M.C., Kelly, J.M., Chapman, C.J., Fairlamb, A.H., and Miles, M.A. (1994). The structure, organization, and expression of the *Leishmania donovani* gene encoding trypanothione reductase. Mol. Biochem. Parasitol. 64:293–301.

Papadopoulou, B., Roy, G. and Ouellette, M. (1994). Autonomous replication of bacterial DNA plasmid oligomers in Leishmania. Mol. Biochem. Parasitol. 65:39–49.

Cruz, A., Titus, R., and Beverley, S.M. (1993). Plasticity in chromosome number and testing of essential genes in Leishmania by targeting. Proc. Natl. Acad. Sci. USA 90:1599–1603.

Charest, H. and Matlashewski, G. (1994). Developmental gene expression in *Leishmania donovani*: differential cloning and analysis of an amastigote stage–specific gene. Mol. Cell. Biol. 14:2975–2984.

Brun and Schönenberger (1979) Acta Trop. 36:289.

Papadopoulou, B., Roy, G., and Ouellette, M. (1992) A novel antifolate resistance gene on the amplified H circle of Leishmania. EMBO J. 11:3601–3608.

Olivier, M., Baimbridge, K.G. and Rainer, N.E. (1992) Stimulus–response coupling in monocytes infected with Leishmania. Attenuation of calcium transients is related to defective agonist–induced accumulation of inositol phosphates. J. Immunol. 148:1188–1196.

Taylor, M.C., Kelly, J.M., Chapman, C.J. Fairlamb, A.H. and Miles, M.A. (1994). The structure, organization and expression of the *Leishmania donovani* gene encoding trypanothione reductase. Mol. Biochem. Parasitol. 64:293–301.

Ryan, K.A., Dasgupta, S., and Beverley, S.M. (1993) Gene, 131:145.

Bernards, A., van der Ploeg, L.H.T., Frasch, A.C.C., Borst, P., Boothroyd, J.C., Coleman., S., and Cross, G.A.M. (1981). Activation of trypanosome surface glycoprotein genes involves a duplication– transposition leading to an altered 3' end. Cell 27:497–505.

(List continued on next page.)

Primary Examiner—Mark Navarro
(74) Attorney, Agent, or Firm—Sim & McBurney (57) ABSTRACT

Attenuated strains of Leishmania are provided in which at least one gene contributing to virulence of the strain and expressed in both the promastigote and amastigote forms of the strain is functionally disabled, such as, by deleting at least a portion of the gene or by mutagenesis of the gene. The attenuated strain may be used for administration to a host to confer protection against disease caused by a virulent Leishmania strain or as a diagnostic reagent.

2 Claims, 9 Drawing Sheets

OTHER PUBLICATIONS

Van der Ploeg L.H.T., Schwartz, D.C., Cantor, C.R., and Borst, P. (1984). Antigenic variation in *Trypanosoma brucei* analysed by electrophoretic separation of chromosome–sized DNA molecules. Cell 37:77–84.

Thomashow, L.S., Milhausen, M., Rutter, W.J., and Agabian, N. (1983) Cell 32:35–43.

White, T.C., Fase–Fowler, F., van Luenen, H., Calafat, J., and Borst, P. (1988). The H circles of *Leishmania tarentolae* are a unique amplifiable system of oligomeric DNAs associated with drug resistance. J. Biol. Chem. 263: 16977–16983.

Thierry, A., Perrin, A., Boyer, J., Fairhead, C. and Dujou, B. (1991), Cleavage of yeast and bacteriophage T7 genomes at a single site using the rare cutter endonuclease I–SceI. Nucleic Acids Res. 19: 189–190.

\* cited by examiner

a-tubulin →

ATTENUATED STRAINS OF LEISHMANIA AND USES THEREOF

REFERENCE TO RELATED APPLICATIONS

This patent application is a divisional of, now U.S. patent application Ser. No. 08/643,751 filed May 6, 1996, now U.S. Pat. No 6,162,638.

FIELD OF INVENTION

The present invention relates to the field of molecular immunobiology and in particular to immunogenic preparations including vaccines comprising attenuated strains of Leishmania.

BACKGROUND OF INVENTION

Parasitic protozoa of the order Kinetoplastidae are the causative agents of several tropical diseases including sleeping sickness by *Trypanosoma brucei*, Chagas by *Trypanosoma cruzi*, visceral (kala-azar) and cutaneous (oriental sore) Leishmaniasis by *Leishmania donovani* and Leishmania major respectively. In particular Leishmania protozoans are the causative agents of human leishmaniasis, which includes a spectrum of diseases ranging from self-healing skin ulcers to fatal visceral infections. Human leishmaniasis is caused by at least thirteen different species and subspecies of parasites of the genus Leishmania. Leishmaniasis has been reported from about eighty countries and probably some 400,000 new cases occur each year. Recently the World Health Organization has reported 12 million people to be infected (ref. 1. Throughout this application various references are referred to in parenthesis to more fully describe the state of the art to which this invention pertains. Full bibliographic information for each citation is found at the end of the specification, immediately preceding the claims. The disclosure of these references are hereby incorporated by reference into the present disclosure. A listing of the references appears at the end of the disclosure).

Untreated visceral leishmaniasis is usually fatal and mucocutaneous leishmaniasis produces mutilation by destruction of the naso-oropharyngeal cavity and, in some cases, death.

In addition a major health problem has been created in areas of high infection when blood is collected for transfusion purposes. Since blood is a carrier of the parasites, blood from an infected individual may be unknowingly transferred to a healthy individual.

The Leishmania protozoans exist as extracellular flagellated promastigotes in the alimentary tract of the sandfly in the free-living state, and are transmitted to the mammalian host through the bite of the insect vector. Once introduced, the promastigotes are taken up by macrophages, rapidly differentiate into non-flagellated amastigotes and start to multiply within the phagolysosomal compartment. As the infected cells rupture, amastigotes subsequently infect other macrophages giving rise to the various symptoms associated with leishmaniasis (refs. 1 and 2).

Leishmaniasis is, therefore, a serious disease and various types of vaccines against the disease have been developed, including live parasites; frozen promastigotes from culture; sonicated promastigotes; gamma-irradiated live promastigotes; and formalin-killed promastigotes treated with glucan (reviewed in, for example ref. 3). However, none of these approaches have provided efficacious vaccines.

Trypanosomatids, among many other metabolic peculiarities, maintain the redox balance of the cell by a mechanism that is completely different from that of their mammalian host. They lack glutathione reductase which in nearly all organisms is responsible for the maintenance of an intracellular reducing environment important for the reduction of disulphides, the detoxification of peroxides and the synthesis of DNA precursors (refs. 4 and 5). Instead, they possess a unique system using as a main thiols, the N2, N8-bis (glutathionyl) spermidine, also named trypanothione [T(SH)2] and the monoglutathionyl spermidine. These conjugates are kept in the reduced state by trypanothione reductase (TR) (refs. 4, 6 and 7). TR is a member of a NADPH-dependent flavoprotein oxidoreductase family and it is structurally and mechanistically related to the human glutathione reductase (GR) (refs. 6 and 8).

Leishmania, during its infective cycle, must survive the rigours of the host's oxidative phagocytic macrophages producing toxic oxygen intermediates. TR and thiols play a vital role in maintaining an intracellular reducing environment and in protecting these parasites against oxidative damage, arising both internally as a result of their aerobic metabolism and externally by the immune response of the mammalian host (refs. 4 and 6).

Leishmania infection may lead to serious disease. It would be advantageous to provide attenuated strains of Leishmania and methods of production thereof, for use as antigens in immunogenic preparations, including vaccines, and the generation of diagnostic reagents.

SUMMARY OF THE INVENTION

The present invention is directed towards the provision of attenuated strains of Leishmania. The attenuated strains are useful for the preparation of immunogenic preparations including vaccines against disease caused by infection by a virulent Leishmania strain and as tools for the generation of immunological and diagnostic reagents.

In accordance with one aspect of the present invention, there is provided an attenuated strain of Leishmania wherein at least one gene of the strain contributing to virulence thereof and expressed in both the promastigote and amastigote stages of the life cycle of the strain has been functionally disabled by, for example, a deletion of at least a portion of the gene or by mutagenesis.

In another aspect of the invention, there is provided an attenuated strain of Leishmania wherein both wild-type copies of a gene of the strain contributing to virulence thereof have been functionally disabled and a third copy of the wild-type gene is present in the chromosome of the strain. The gene contributing to the virulence of the strain in this aspect of the invention may be one expressed in both the promastigote and amastigote stages of the life cycle of the strain.

The gene may contribute to the ability of the strain to infect or survive within macrophages and, in a particular embodiment, may encode trypanothione reductase. The attenuated Leishmania strain may be selected from the group consisting of *Leishmania donovani, Leishmania braziliensis, Leishmania tarentolae, Leishmania major, Leishmania mexicana, Leishmania tropica* and *Leishmania aethiopica*.

In a further aspect, the present invention provides an immunogenic composition comprising the attenuated strains as provided herein. The immunogenic composition may be formulated as a vaccine for in vivo administration to a host, such as a primate including humans, to confer protection against disease caused by a virulent strain of Leishmania, including *Leishmania donovani, Leishmania braziliensis,*

*Leishmania tarentolae, Leishmania major, Leishmania mexicana, Leishmania tropica* and *Leishmania aethiopica*.

In an additional aspect, the invention provides a method of generating an immune response in a host, such as, a primate including humans, comprising administering thereto an immunoeffective amount of the immunogenic composition, as provided herein. In a particular aspect, the immunogenic composition may be formulated as a vaccine for in vivo administration to the host to confer protection against disease caused by a virulent strain of Leishmania, including *Leishmania donovani, Leishmania braziliensis, Leishmania tarentolae, Leishmania major, Leishmania mexicana, Leishmania tropica* and *Leishmania aethiopica*.

In yet an additional aspect, there is provided a method for producing a vaccine for protection against a disease caused by infection by a virulent strain of Leishmania, including *Leishmania donovani, Leishmania braziliensis, Leishmania tarentolae, Leishmania mexicana, Leishmania tropica* and *Leishmania aethiopica*, and comprising administering the immunogenic composition as provided herein to a test host to determine an amount and frequency of administration thereof to confer protection against disease caused by infection by the Leishmania parasite and formulating the immunogenic composition in a form suitable for administration to a treated host, including humans, in accordance with said determined amount and frequency of administration.

In a further aspect of the invention, there is provided a method of forming an attenuated strain of Leishmania, which comprises identifying a gene of a Leishmania strain contributing to the virulence thereof and expressed in both the promastigote and amastigote stages of the life cycle of the strain, and functionally disabling the gene.

These virulence genes may be functionally disabled by, for example, deletion or mutation, including insertional mutagenesis and, furthermore, the wild-type Leishmania gene may be replaced by the functionally disabled gene. The virulence genes may be functionally disabled by, for example, replacing the gene by a selectable antibiotic resistance gene by homologous recombination following transformation of the Leishmania organism with a fragment of DNA containing the antibiotic resistance gene flanked by 5'- and 3'- non-coding DNA sequences.

This method can be used to generate the attenuated variants of Leishmania and the residual pathogenicity of the attenuated variants can be assessed in mice and hamsters. Deletion of the genes that are selectively expressed results in an attenuated strain which cannot survive in humans but generates a protective immune response. Attenuated strains of Leishmania as provided herein would be useful as live vaccines against the diseases caused by Leishmania.

Advantages of the present invention include the provision of safe and attenuated strains of Leishmania for the preparation of immunogenic compositions including vaccines and for the generation of immunological and diagnostic reagents.

BRIEF DESCRIPTION OF THE DRAWINGS

The present invention will be further understood from the following description and specific Examples with reference to the Figures, in which.

GENERAL DESCRIPTION OF THE INVENTION

Figure 1A:
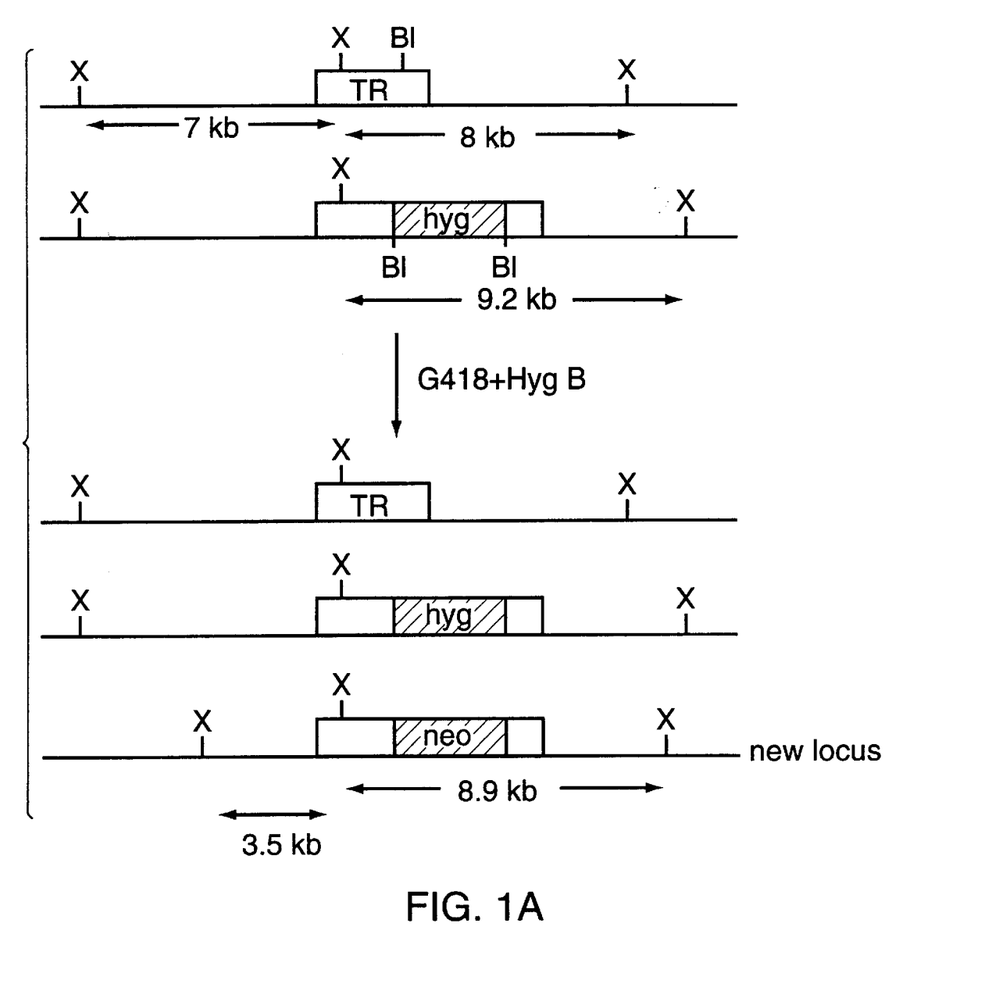
FIG. 1(A) shows schematically the inactivation of the two copies of the trypanothione reductase gene in *Leishmania donovani;*
Figure 1B:
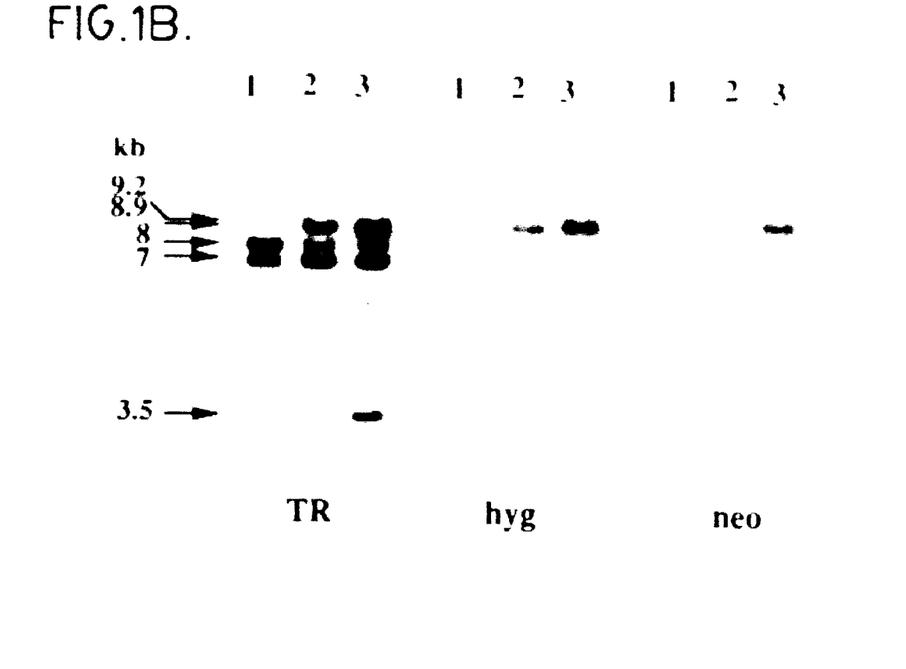
FIG. 1(B) shows a Southern blot analysis of wild-type *Leishmania donovani* and strains having one or two of the trypanothione reductase genes deleted therefrom.
Figure 1C:
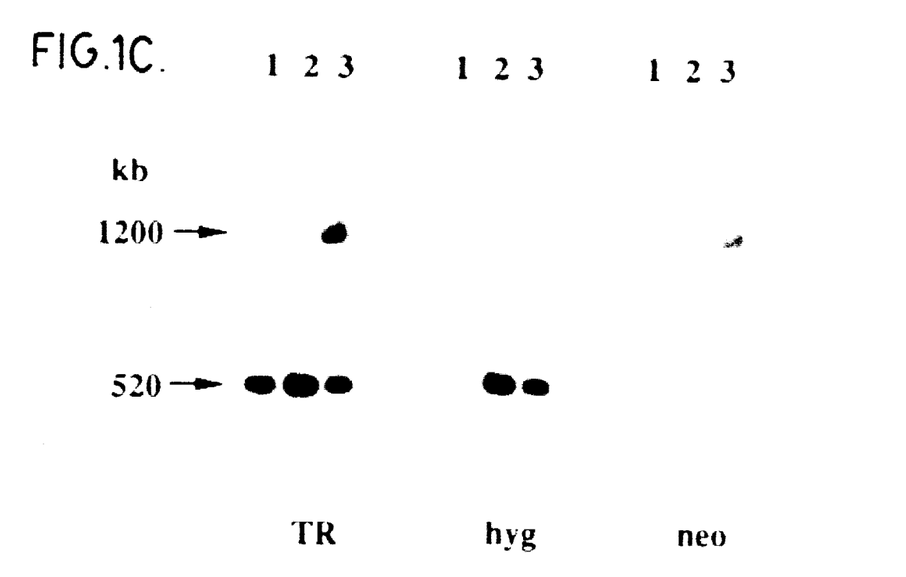
FIG. 1(C) shows a molecular karyotype of diploid and triploid *Leishmania donovani* trypanothione reductase gene transfectants.

Referring to FIG. 1, there is schematically illustrated the inactivation of trypanothione reductase (TR) genes in *Leishmania donovani*. The TR gene is a single copy gene in the Leishmania genome and it is located on a 520 kb chromosome (ref. 9, 1994; FIG. 1C). Since the Leishmania genome is diploid and no sexual crosses have been achieved, two successive rounds of gene targeting are necessary to disrupt such a single copy gene. To inactivate both alleles of the TR gene of *L. donovani* by gene disruption mediated by homologous recombination, a 1.2 kb fragment entirely within the TR coding sequence was amplified by PCR. This fragment was inserted into pSP72 vector. The neomycin phosphotransferase (neo) and the hygromycin phosphotransferase (hyg) expression cassettes (ref. 10) were introduced into the unique BalI site of the TR gene, at 387 bp from the 3'-end of the PCR generated fragment (see FIG. 1A). In a first round of targeting, the TR-hyg replacement construct was transfected into *L. donovani*. Cells growing in the presence of hygromycin B were cloned on semi-agar plate and the DNA of clones were digested with XhoI and analyzed by Southern blots hybridized to specific TR and hyg probes (see FIG. 1(B)). A schematic drawing of the TR locus in L. donovani with the TR gene and restriction sites (X, XhoI, Bl, BalI) is shown in FIG. 1(A). Upon integration of the hyg or neo genes at the homologous locus, the genomic 8 kb XhoI fragment would increase to 9.2 kb and to 8.9 kb, respectively. The 3.5 kb X-X' corresponds to a new restriction fragment generated following genomic rearrangements to translocation of a part of the TR locus on a 1200 kb chromosome.

FIG. 1(B) shows a Southern blot analysis of *L. donovani* WT and TR single and double replacement mutants. DNAs were digested with XhoI, electrophoresed through an agarose gel and hybridized independently with TR, hyg and neo specific probes. Lanes 1, *L. donovani* WT strain; 2, *L. donovani* TR/hyg single knockout strain and 3, *L. donovani* TR/hyg/neo double targeted mutant. Two XhoI fragments of 7 and 8 kb are recognized by the TR probe in wild type (WT) *L. donovani* (FIG. 1(A) and 1(B), lane 1). Upon the integration of the hyg gene into the TR locus the 8 kb restriction band increased by 1.2 kb to yield a 9.2 kb fragment whereas the 7 kb fragment remained unchanged. The presence of a 8 kb band in these clones corresponds to the second non-targeted TR allele (FIG. 1(B), lane 2). Further hybridization of the 9.2 kb fragment to a hyg probe (FIG. 1(B), lane 2) confirmed the presence of the expected heterozygous replacement.

A clone of the TR/hyg transfectant was then used for the second round of targeting using the TR-neo replacement construct (FIG. 1(A)). Transfectants resistant to G418 and hygromycin B were obtained and clones were analyzed by hybridization using probes specific for TR, neo and hyg. The neo gene was integrated into the TR locus as an XhoI fragment of the expected size of 8.9 kb was obtained following hybridization to a neo probe (see FIG. 1(B), lane 3). Although the neo and hyg replacements took place as expected, one TR allele remained intact since the genomic 8 kb XhoI fragment was also present in the double targeted mutant (FIG. 1(B), lane 3). Moreover, a novel 3.5 kb XhoI fragment hybridizing to the TR probe was detected in this transfectant (FIG. 1(B), lane 3) indicating that this novel band is a result of genomic rearrangements that occurred relatively close to the TR gene.

Figure 2A:
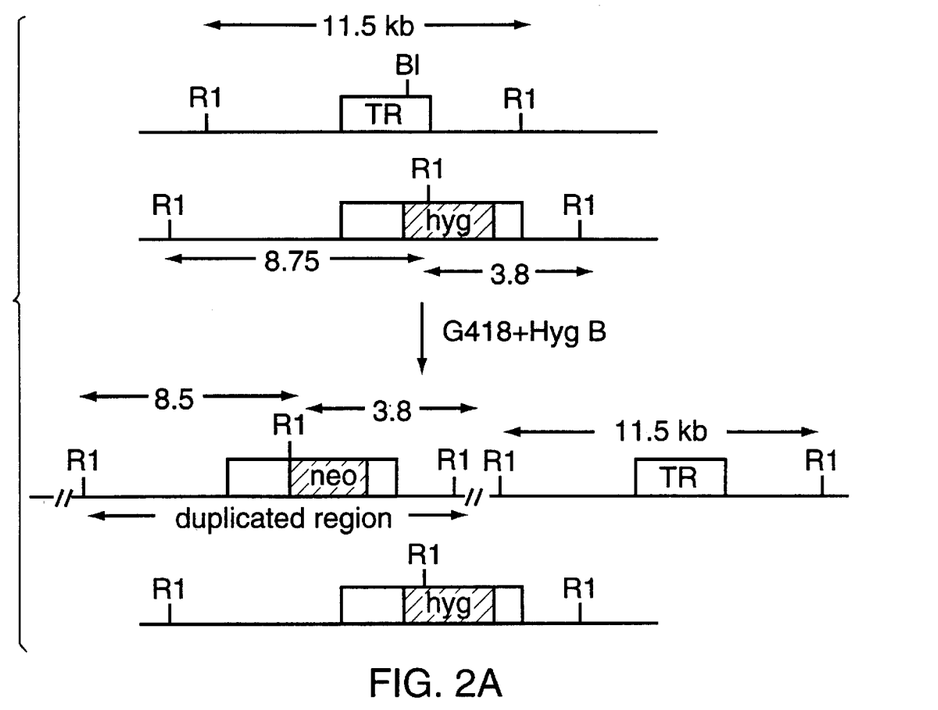
FIG. 2(A) shows schematically the inactivation of trypanothione reductase gene in *Leishmania tarentolae;*

To look at how this novel fragment has arisen, chromosomes of the TR/hyg/neo transfectant were resolved by CHEF electrophoresis and the blot was hybridized with the appropriate probes. In FIG. 1(C), there is shown a molecular karyotype of diploid and triploid *L. donovani* TR transfectants. Chromosomes were separated by pulsed-field gel electrophoresis using a Biorad CHEF-DR III apparatus at 5 V/cm, 120° separation angle and switch times varying from 35–120 for 27 h. Lanes 1: *L. donovani* WT strain; 2: *L. donovani* TR/hyg single knockout strain; and 3: *L. donovani* TR/hyg/neo double targeted mutant. Blots were hybridized with TR, hyg and neo-specific probes as shown. In addition to a 520 kb chromosome on which the TR gene is normally located, a new chromosome of approximately 1200 kb hybridized to a TR specific probe (FIG. 1(C), lane 3). The third allele present in the new chromosomal location correspond to the one targeted by the neo gene (see FIG. 1(C), lane 3), thus leaving an intact TR allele in the initial chromosomal location (520 kb). Therefore this attempt to generate a TR null mutant in *L. donovani* has failed and, in an additional independent transfection, we were also unable to generate a null mutant as the locus became triploid. This may suggest that the TR gene is an essential gene. To test whether the polyploidy of the TR locus occurred only in a pathogenic virulent strain as previously described for the dhfr-ts gene of one virulent *L. major* strain (ref. 11), we have attempted to disrupt the TR gene of the non-pathogenic lizard strain *L. tarentolae*. Thus, referring to FIG. 2, there is schematically illustrated the inactivation of the TR gene in *Leishmania tarentolae*. Constructs derived from one species are not appropriate for the targeting of genes of another species of Leishmania. Therefore, the TR gene of *L. tarentolae* was amplified by PCR and the hyg and neo expression cassettes were cloned into the BalI site of the PCR fragment and transfections were performed to inactivate both alleles of the *L. tarentolae* TR gene. Referring to FIG. 2A there is a schematic drawing of the TR locus in *L. tarentolae*. Following integration of the hyg gene at the homologous locus, two additional EcoRI (RI) fragments of 8.75 and 3.8 kb would be generated and after the neo insertion two EcoRI fragments of 8.5 and 3.8 kb.

Figure 2B:
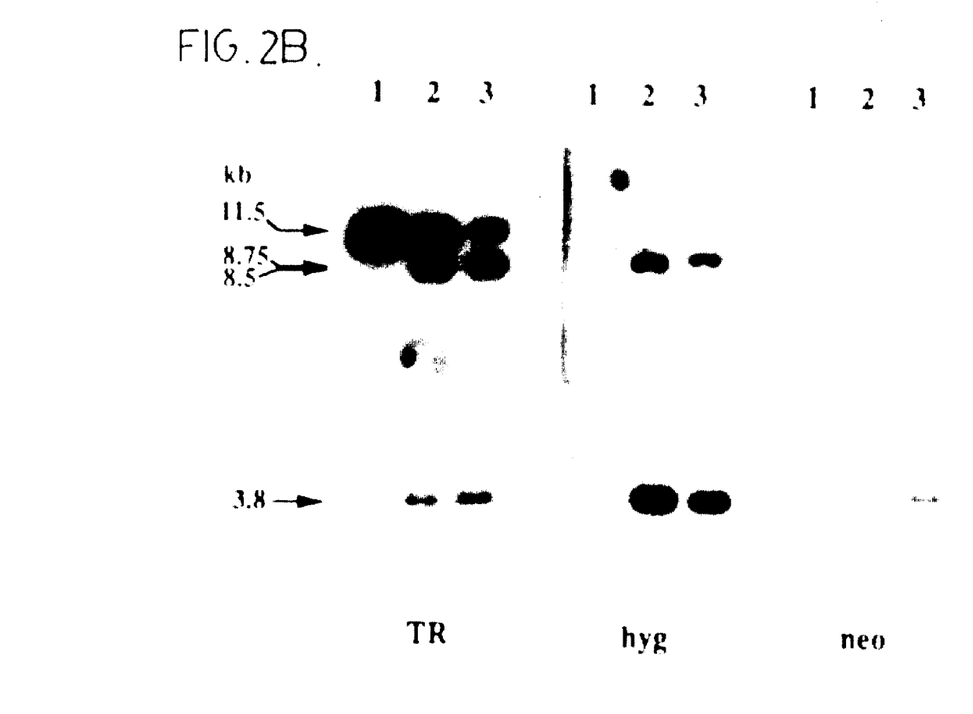
FIG. 2(B) shows a Southern blot analysis of wild-type *Leishmania tarentolae* and strains having one or two copies of the trypanothione reductase gene deleted therefrom.
Figure 2C:
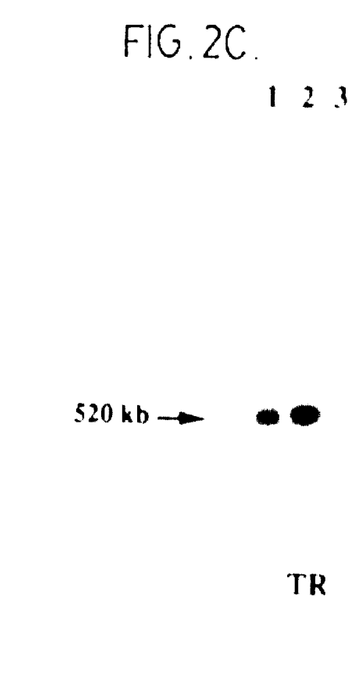
FIG. 2(C) shows a molecular karyotype of diploid and triploid *Leishmania tarentolae* trypanothione reductase gene transfectants.

FIG. 2(B) shows a Southern blot analysis of WT, single targeted and double targeted TR *L. tarentolae* mutants. DNAs were digested with EcoRI, electrophoresed through an agarose gel and hybridized with TR, hyg and neo specific probes. Lanes 1: *L. tarentolae* TarII WT strain 2: *L. tarentolae* TR/hyg and 3: *L. tarentolae* TR/hyg/neo. Disruption of one TR allele, by replacement with a TR-hyg fragment, led to the generation of two expected additional EcoRI bands of 8.75 and 3.8 kb as well as the intact allele of 11.5 kb is indicated by Southern blot analysis of transfectant's DNA hybridized to TR and hyg probes (FIG. 2(B), lane 2). Upon integration of the TR-neo construct into the remaining intact TR allele of the *L. tarentolae* TR/hyg strain, the expected EcoRI fragments of 8.5 and. 3.8 kb hybridized to the TR probe and only the 3.8 kb band hybridized to the neo probe as expected but nevertheless one TR allele was present (FIG. 2(B), lane 3). Two further independent transfections into *L. tarentolae* ended up also with a TR triploidy. Contrary to *L. donovani*, no additional bands hybridizing to TR observed, and both disrupted and wild type TR alleles were located on a same chromosome of the same size (FIG. 2(C)).

Figure 3A:
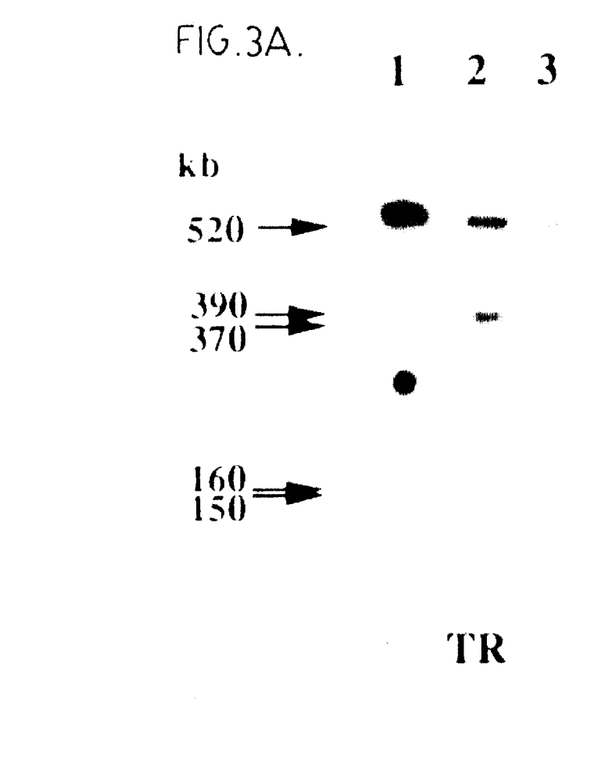
FIG. 3(A) is a CHEF blot of chromosomes of the diploid and triploid TR *L. tarentolae* transfectants hybridizing to TR, neo and hyg probes.
Figure 3B:
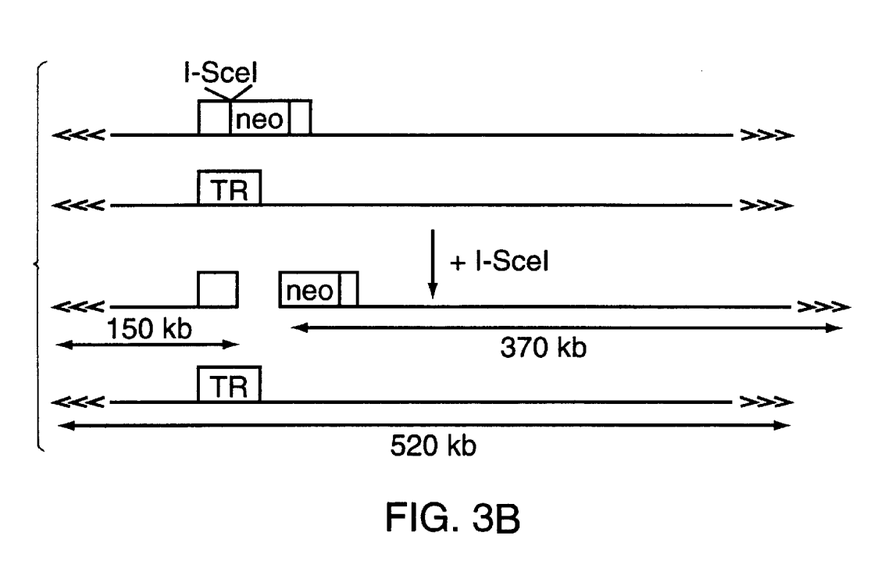
FIG. 3(B) shows the integration of the I-SceI recognition sequence into TR gene together with a neo expression cassette.
Figure 3C:
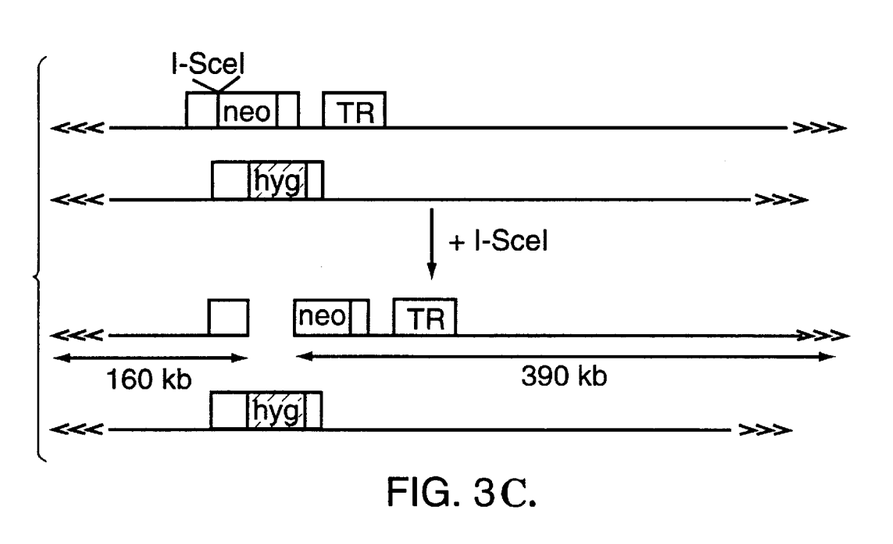
FIG. 3(C) shows the generation of the third TR allele in triploid L. tarentolae mutant.

To exclude the possibility of preexisting triploidy of the TR gene in *L. tarentolae* and to map the third TR allele with respect to the TR normal chromosomal location we have integrated into the TR locus a neo cassette containing a unique sequence corresponding to the recognition site of I-SceI endonuclease. Referring to FIG. 3, there is shown the integration of the endonuclease I-SceI into the TR locus to explain TR triploidy in *L. tarentolae*. FIG. 3A shows a CHEF blot of chromosomes of the diploid and triploid TR *L. tarentolae* transfectants hybridizing to TR, neo and hyg probes. Upon digestion with the I-SceI endonuclease, three chromosomal fragments would be generated as shown in Lanes 1: *L. tarentolae* WT 2: TR/neo-SceI digested with endonuclease I-SceI 3: and TR/hyg/neo-SceI digested with I-SceI. I-SceI has an 18-bp recognition sequence (ref. 22). Following digestion of the single TR/neo knockout transfectant with the endonuclease I-SceI the 520 kb chromosome was fragmented in two pieces one of 150 and the second of 370 kb as detected by hybridization of a CHEF blot with the TR probe (FIG. 3(A), lane 2). Only the largest fragment of 370 kb hybridized to a neo probe as expected. In FIG. 3(B), there is illustrated a schematic drawing of the integration of the I-SceI recognition sequence into the TR gene together with a neo expression cassette. Following I-SceI digestion three fragments should be generated; one of 520 kb corresponding to the intact TR carrying chromosome and two fragments resulted from the in vitro fragmentation of the second chromosomal allele within the unique I-SceI integration. FIG. 3(C) shows the generation of the third TR allele in the triploid *L. tarentolae* mutant supported by the results of the I-SceI digest. A region of approximately 30 kb was duplicated providing the TR triploidy. This increased the size of the two I-SceI chromosomal fragments to 160 and 390 kb, respectively, instead of 150 and 370 kb as shown in panel B. In a double targeted mutant where one TR allele was disrupted by hyg and the second by the neo-I-SceI cassette two fragments of slightly different sizes of 160 and 390 kb were hybridized to a TR probe (FIG. 3(A), lane 3 and FIG. 3(C)) indicating that approximately 30 kb were added in the neo targeted chromosome during rearrangement leading to the TR polyploidy.

Figure 4A:
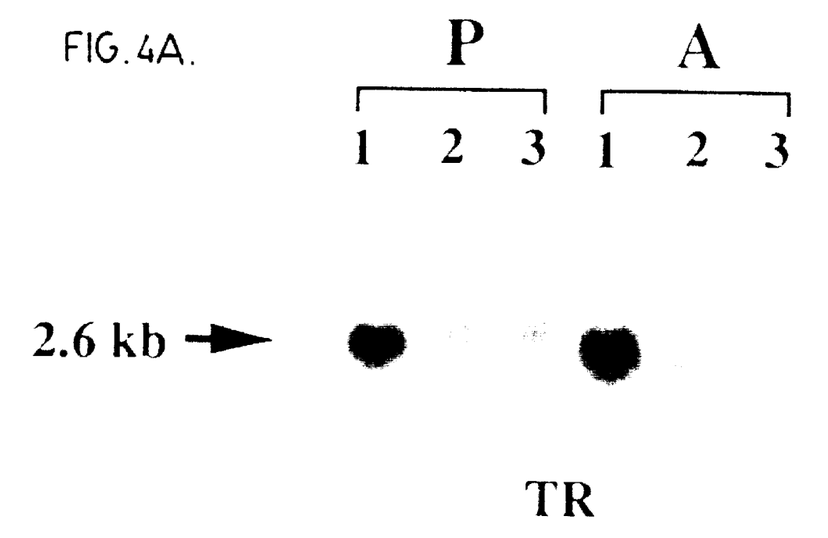
FIGS. 4A and 4B are a Northern blot to show trypanothione reductase mRNA expression in wild-type and *Leishmania donovani* trypanothione reductase inactivated mutants.
Figure 4B:
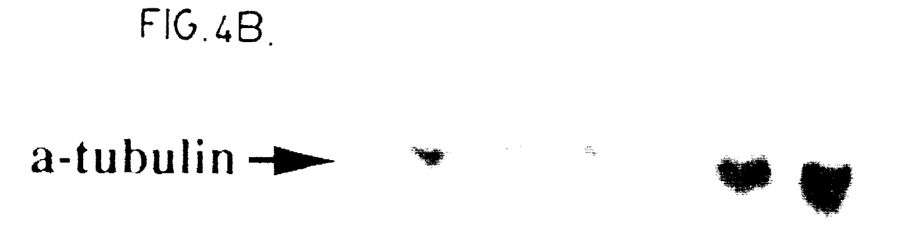

The single and double targeted TR mutants generated by gene disruption described herein contained one intact TR allele. To examine the effect of the decrease in TR copy number to TR expression, mRNA levels in both promastigote and amastigote stages of the parasite were examined. FIG. 4 shows TR mRNA expression in the control and TR single and double *L. donovani* targeted mutants. In FIG. 4(A) total RNAs isolated from the promastigote and amastigote stages of *L. donovani* control and transfectants were hybridized with a TR specific probe. Each track contained 5 µg of RNA. Lanes 1, *L. donovani*; WT; 2, TR/hyg single knockout and 3, TR/hyg/neo double targeted mutant. In FIG. 4(B), the same blot was stripped off and re-hybridized with the *T. brucei* α-tubulin probe to monitor the amount of RNA layered on each lane. This Northern blot analysis using a TR specific probe showed that *L. donovani* parasites either with the TR/hyg or the TR/hyg/neo background have much lower RNA levels compared to the WT (FIG. 4 (A)). No differential expression of TR in the mutants was noted between promastigotes and amastigotes (see FIG. 4 (A)). The amastigote's total RNA was checked by hybridization with an amastigote specific probe, the gene A2 (ref. 12). The amount of RNA loaded was compared with a tubulin probe (FIG. 4(B)).

Figure 5A:
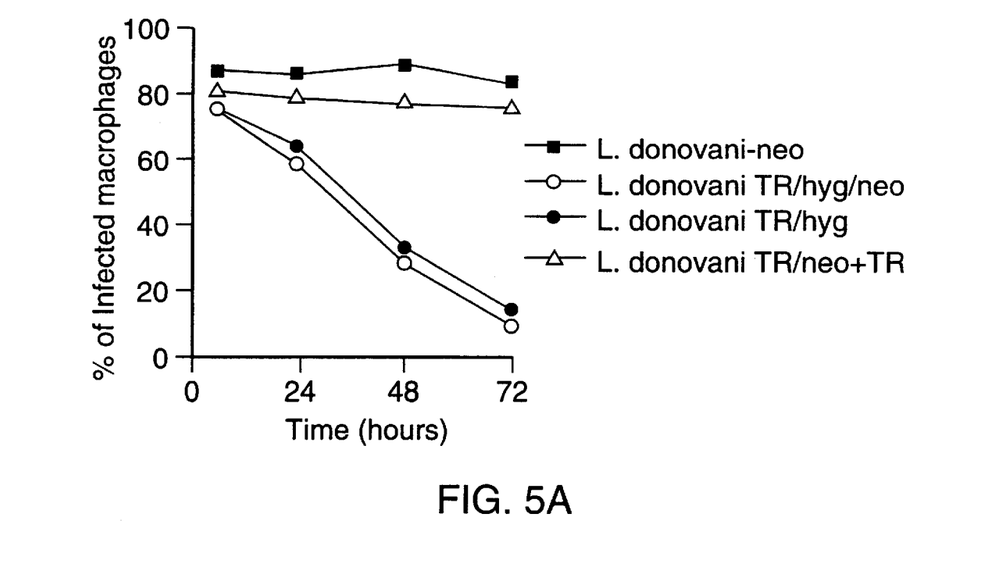
FIGS. 5A and 5B shows the ability of *Leishmania donovani* trypanothione reductase disrupted mutants to infect human macrophages.
Figure 5B:
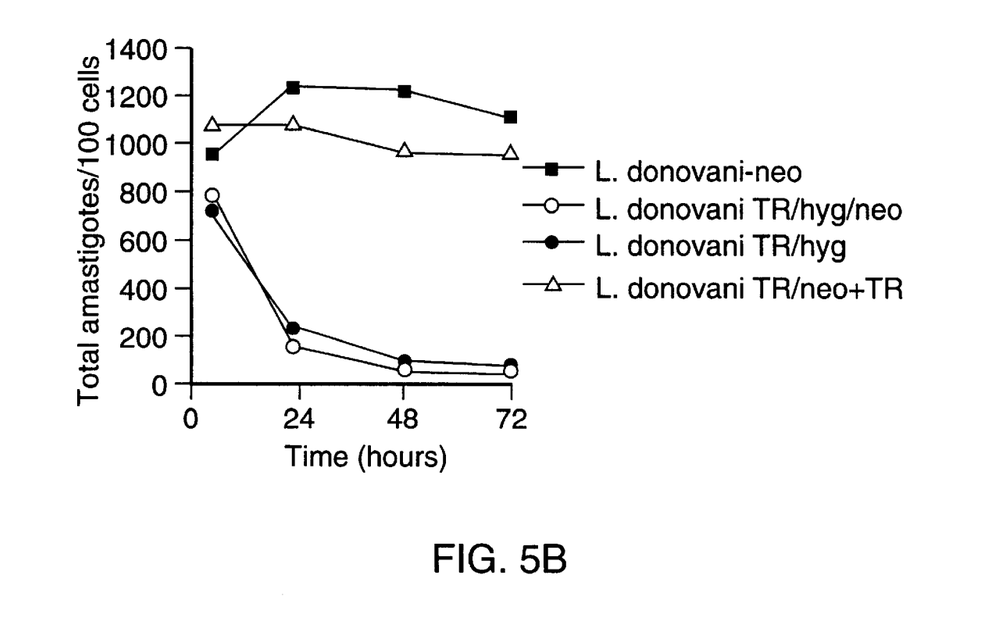

To determine whether decreased levels of mRNA in the disruption mutants correlated with decreased TR activity we have measured enzymatic activities in control and TR mutant strains. A significant decrease on TR enzymatic activity was detected in the single and the double targeted TR mutants as shown in Table I. Reduced TR activity did not affect the growth of Leishmania in culture media and did not influence the transformation to amastigotes in vitro. In *L. donovani* TR/hyg and TR/hyg/neo targeted mutants, the TR activity was 2.7-fold lower than in control *L. donovani* WT cells (Table 1). A 4-fold decrease in TR activity was detected in the *L. tarentolae* TR/hyg/neo transfectant (see Table 1). The ability of the TR-disruption mutants to survive within human macrophages was examined using an in vitro infection system. Both the single *L. donovani* TR/hyg and the double targeted TR/hyg/neo mutants were tested. FIG. 5 shows the infectivity of *L. donovani* TR replacement mutants toward human macrophages. Cells from stationary phase of *L. donovani* control and the single and double TR replacement mutants were harvested and counted with the Neubauer improved counting chamber. Human macrophages ($5 \times 10^4$ cells/well) were incubated with Leishmania parasites (20:1, parasite-to-cell ratio) for 6 hours. After this initial incubation, free parasites were washed and fresh media was added to the wells and incubated for 24, 48 and 72 hours. At these fixed time points cell cultures were dried and stained with Diff Quick in order to determine the level of infection. The panel in FIG. 5(B) corresponds to the total number of amastigotes in 100 macrophage cells and the panel in FIG. 5(A) to the percentage of infected macrophages with time. ■ *L. donovani*-neo (control strain with a plasmid carrying the neo gene); ○ *L. donovani* TR/hyg, ▲ *L. donovani* TR/hyg/neo, □ *L. donovani* TR/neo+TR. The average and standard deviation of four independent experiments are shown. The intracellular survival of the amastigotes of the *L. donovani* TR/hyg and TR/hyg/neo mutants inside human monocytes differentiated to macrophages was measured by microscopic examination after 24, 48 and 72 hours post-infection and compared to *L. donovani* transfected with a neo-containing plasmid as a control. Values were expressed either as the percentage of macrophages that were infected by *L. donovani* or as the number of amastigotes within 100 macrophages. A very significant decrease of the percentage of macrophages infected with the double targeted TR mutant was observed as soon as 24 hours following the infection (FIG. 5(A)). Indeed, although the infection rate was maintained throughout the experiment for the control Leishmania transfectant, the infection rate of the TR/hyg and TR/hyg/neo decreases steadily to reach only 12% at 72 hours (FIG. 5(A)). Similarly, the number of *L. donovani* TR/hyg/neo amastigotes per macrophage cell has drastically decreased from 15.5 amastigotes/cell at 6 hours infection to below 1 amastigote/cell after 72 hours (see FIG. 5(B)). The single TR/hyg mutant showed a similar phenotype with respect to intracellular survival (FIG. 5(B)). The loss of a single TR allele has dramatic consequences for the intracellular viability of *L. donovani*. To prove that the observed phenotype was due solely to the disruption of TR, we have transfected into *L. donovani* TR/neo a cosmid containing the entire TR gene of *L. donovani* infantum. This recombinant strain overexpressing TR regained completely its ability to survive inside macrophages to WT levels (FIG. 5) clearly indicating that the loss of one copy of TR was responsible for the decrease intracellular survival of the mutants.

Figure 6A:
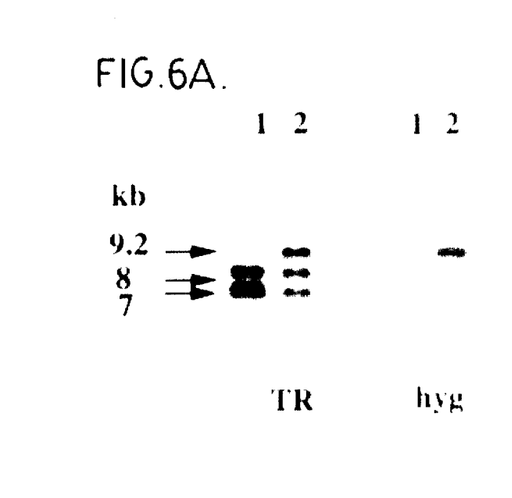
FIG. 6(A) shows a Southern blot of the deletion of the trypanothione reductase gene from *Leishmania major* by gene targeting.
Figure 6B:
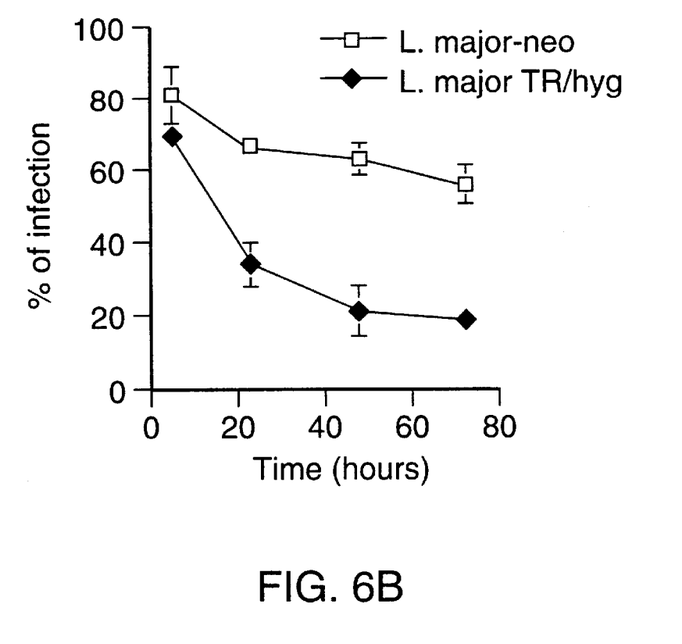
FIG. 6(B), consisting of two panels, shows the ability of *Leishmania major* trypanothione reductase inactivated mutants to infect human macrophages.
Figure 6C:
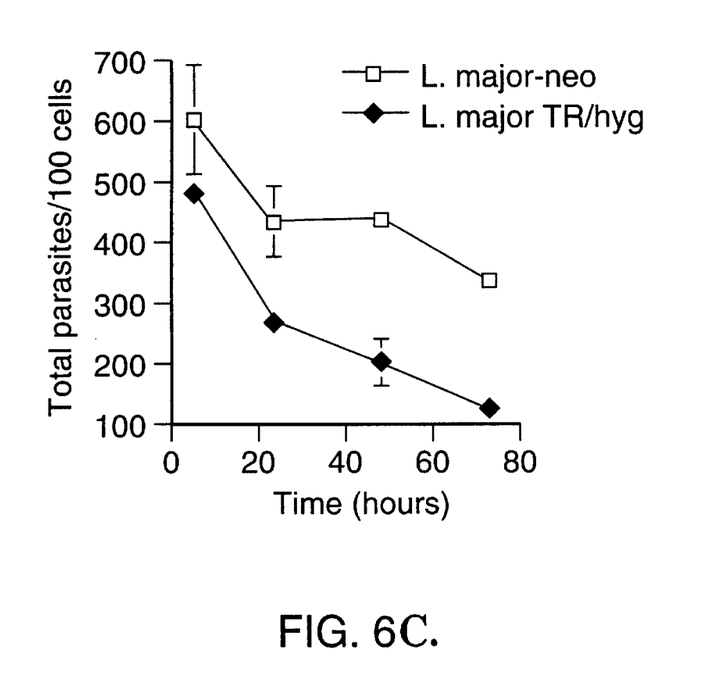
FIG. 6(C) shows the ability of *Leishmania major* trypanothione reductase inactivated mutants to infect human macrophage expressed as the total number of amastigotes in 100 macrophage cells.

To test whether the results observed in *L. donovani* would be paralleled in other pathogenic species, we have amplified a fragment of the *L. major* TR gene by PCR. The hyg expression cassette was cloned into the BalI site of the PCR fragment and this TR-hyg targeting construct was transfected into *L. major*. FIG. 6 shows the generation of an *L. major* replacement TR mutant by gene targeting and its infectivity within human macrophages. FIG. 6(A) Southern blot analysis of total DNAs from *L. major* WT (lane 1) and *L. major* TR/hyg (lane 2) digested with XhoI and hybridized to TR and hyg specific probes. FIG. 6(B) shows macrophage infection in vitro with *L. major*. This was done as described above. The left panel corresponds to the total number of amastigotes in 100 macrophage cells and the right panel to the percentage of infected macrophages with time. ○ *L. major*-neo (control strain); □ *L. major* TR/hyg, single knockout. The average and standard deviation of four independent experiments are shown. The XhoI restriction sites were identical between *L. major* and *L. donovani* and upon the integration of the hyg gene, one TR allele was disrupted (9.2 kb fragment) (FIG. 6A, lane 2). Less TR activity was found in this mutant as it was the case for the other Leishmania TR inactivated mutants (Table 1). The *L. major*/hyg disruption mutant was further tested for its capacity to infect human-macrophages. As observed for *L. donovani*, the *L. major* transfectant missing one TR allele showed a decrease in parasite infectivity. Indeed, a sharper decrease of the infectivity was observed compared to *L. major* control transfectant and 2.5 amastigotes/cell were detected at 72 hours post-infection, a 4-fold difference with control cells (see FIG. 6B).

The phenotype of the TR mutants generated in this study indicate that these parasites are suitable for live vaccine development.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, immunology and fermentation technology used but not explicitly described in the disclosure and these Examples are amply reported in the scientific literature and are well within the ability of those skilled in the art.

Example 1

This Example describes the culturing and transfection of Leishmania.

The *Leishmania tarentolae* strain Tar II has been described previously (ref. 21) and the *Leishmania major* 50122 and *Leishmania donovani* 50212 strains were obtained from the ATCC. All strains were grown in SDM-79 medium (ref. 13), supplemented with 10% fetal bovine serum (FBS) (Multicell, Wisent Inc.) and 5 µg/mL of hemin. Two to 3 µg of linearized DNA from targeting constructs purified from LMP agarose (Gibco-BRL) were used for transfections into Leishmania cells for electroporation as described previously (ref. 14). Transfectants were selected with 40 µg/mL of G-418 (Geneticin, Gibco-BRL), or 80 µg/mL of hygromycin B (CalBiochem). Murine macrophage cell line J774, obtained from ATCC, was cultured in Dulbecco's modified Eagle's medium (D-MEM, Gibco-BRL), supplemented with 10% FBS, L-glutamine (2mM), penicillin G (100 U/ml) and streptomycin (100 µg/ml). Human peripheral blood monocytes were isolated from heparinized venous blood of normal donors by the Canadian Red Cross. Cells were centrifuged over Ficoll-Paque gradient (Pharmacia) as previously described (ref. 15). After several washes, cells were resuspended in RPMI 1640 medium (Gibco-BRL) containing 10% of human serum (Gibco-BRL). In order to differentiate monocytes into macrophages, $3\times10^6$ peripheral blood leukocytes, counted using trypan blue, were adhered and cultured for 5 days at 37° C. in 5% $C_2$/95% air in a humidified atmosphere to allow for transformation. To transform *Leishmania donovani* promastigotes into amastigotes in vitro, the parasites were grown at room temperature in SDM medium in which HEPES were replaced by MES to adjust the pH to 5.0, and then switched overnight to 37° C. in 5% $CO_2$ atmosphere (ref. 12).

Example 2

This Example describes techniques of recombinant DNA and the construction of targeting constructs.

A large portion of the trypanothione reductase (TR) coding region (85% of the TR gene from nucleotide 153 to 1406) from L. tarentolae, *L. donovani* donovani TR and *L. major* total DNAs was amplified by PCR using degenerated oligonucleotide primers derived from the *L. donovani* TR coding sequence (ref. 16). The HpaI-SacI PCR products (1.2 kb for the *L. donovani* and *L. tarentolae* and 1.3kb for the *L. major*) were subcloned into SacI-SmaI sites of pSP72 vector (Promega). To make the TR gene knockout constructs, the neomycin phosphotransferase (neo) and hygromycin phosphotransferase (hyg) cassettes (ref. 10) were introduced as SmaI-EcoRV fragments into the unique BalI-site of the TR gene. For the TR gene of *L. tarentolae* a neo-I-SceI cassette was introduced instead of a neo cassette. A cosmid clone containing the entire TR coding region and flanking sequences necessary for its expression was isolated by screening a *L. donovani* infantum genomic cosmid library made in the vector CL-hyg (ref. 17) and gridded on high density filters with an *L. donovani* TR specific probe. The TR cosmid clone was transfected into *L. donovani* TR/neo single knockout strain to test for the specificity of the TR-mutant phenotype.

For hybridization studies, total genomic DNA from Leishmania was prepared as described (ref. 18), digested with XhoI or EcoRI, resolved on 0.7% agarose gels and, transferred to nylon membrane (Hybond-N, Amersham). Total RNAs from *Leishmania donovani* WT and transfectants from both promastigote and amastigote stages were prepared using Trizol (Gibco BRL). Southern and Northern blots, hybridizations and washing conditions were done following standard procedures. Intact Leishmania chromosomes were prepared from Leishmania cells harvested during mid to late log-phase, washed and lysed in situ in 1% low melting agarose plugs as previously described (ref. 19). For digestion of the plugs with endonuclease I-SceI the conditions used were according to the suppliers instructions (Boehringer Mannheim). The blocks were loaded directly into the wells of 1% agarose gel and sealed in place. Leishmania chromosomes were separated by pulsed-field gel electrophoresis using a Bio-Rad CHEF-DR III apparatus, stained with ethidium bromide, and transferred to nylon membrane for Southern blot hybridization. Blots were hybridized with radiolabelled probes prepared by randomly primed synthesis with Klenow DNA polymerase and [$\alpha$-$^{32}$p] dATP. The probes used correspond to TR, hyg and neo coding sequences made by PCR, to the $\alpha$-tubulin gene of T. brucei (ref. 20) and to the A2 amastigote gene (ref. 12).

Example 3

This Example describes the in vitro infection of macrophages.

The capacity of the Leishmania TR mutants to infect murine and human macrophages in vitro was tested in comparison to control Leishmania-neo transfectant, as follows. Murine and human macrophages were seeded (200 µl per well, $5\times10^4$ cells/mL) into 8 wells chamber slides, and were infected with parasites, at a parasite to cell ratio of 20:1 for a period of 6 hours. Following this incubation, the non-engulfed parasites were removed by 3 to 5 washes with warm medium and chambers were replenished with 500 µL of fresh culture medium. The level of infection was determined at 6, 24, 48 and 72 hours by optical microscopy examination following Diff Quick staining of cell preparations.

Example 4

This Example describes the trypanothione reductase enzyme assay.

The preparation of cell-free extracts to measure the TR enzymatic activities in wild type and TR disrupted transfectants was done as follows. $2\times10^8$ Leishmania cells were harvested at mid to late log-phase by centrifugation. Cells were washed twice in PBS and after a second centrifugation were resuspended in 0.35 mL of freshly prepared lysis buffer (10 mM potassium phosphate pH 7.2, 10 mM EDTA, 1 mM DTT, 1% Triton X-100, 5 mM benzamidine, 5 mM phenanthroline, 0.1 mM phenyl-methyl-sulphonyl fluoride (PMSF)). Lysis was completed by a freeze/thaw procedure repeated 3 times. TR activity was assayed spectrophotometrically by monitoring substrate dependent oxidation of NADPH at 340 nm using alanine aminotransferase as an internal control (ref. 6).

SUMMARY OF THE DISCLOSURE

In summary of this disclosure, the present invention provides novel attenuated strains of Leishmania in which at least one gene contributing to virulence and expressed in both the promastigote and amastigote stages of the life cycle of the strain is functionally disabled, such as by deleting at least a portion of the gene or by mutagenesis of the gene. Modifications are possible within the scope of this invention.

TABLE I

Trypanothione reductase (TR) activity in Leishmania cells

| Cells | TR genotype | TR (U/mg) | Aat[1] (U/mg) | Ratio TR/Aat |
|---|---|---|---|---|
| L. donovani | TR/TR | 0.212 ± 0.023 | 0.117 ± 0.007 | 1.81 |
| L. donovani | TR/hyg | 0.090 ± 0.005 | 0.112 ± 0.023 | 0.80 |
| L. donovani | TR/hyg/neo | 0.077 ± 0.016 | 0.097 ± 0.003 | 0.79 |
| L. major | TR/TR | 0.437 ± 0.041 | 0.337 ± 0.022 | 1.30 |
| L. major | TR/hyg | 0.096 ± 0.005 | 0.114 ± 0.002 | 0.84 |
| L. tarentolae | TR/TR | 0.196 ± 0.012 | 0.052 ± 0.008 | 3.77 |
| L. tarentolae | TR/hyg/neo | 0.051 ± 0.019 | 0.072 ± 0.003 | 0.71 |

[1]Alanine aminotransferase used as an internal control.

REFERENCES

1. WHO, Tropical Disease Report, 1989. pp. 85–92.
2. Turco, S. J. and Descoteaux, A., 1992. The lipophosphoglycan of Leishmania parasites. Annu. Rev. Microbiol. 46:65–94.
3. Modabber, F. 1989. Experiences with vaccines against cutaneous leshmaniasis: of men and mice. Parasitol. 98:S49–S60.
4. Fairlamb, A. H., Blackburn, P., Ulrich, P., Chait, B. T. and Cerami, A. (1985) Trypanothione: a novel bis (glutathionyl) spermidine cofactor for glutathione reductase in trypanosomatids. Science 227:1485–1487.
5. Schirmer, R. H., and Schulz, G. E. (1987) in: Pyridine Nucleotide Coenzymes, Part B. Coenzymes and Cofactors, vol. 2, Wiley, New York, pp. 333–379.
6. Shames, S. L., Fairlamb, A. H., Cerami, A., and Walsh, C. T. (1986) Purification and characterization of trypanothione reductase from *Crithidia fasciculata*, a newly discovered member of family of disulphide-containing flavoprotein reductases. Biochemistry 25: 3519–3526.
7. Fairlamb, A. H., and Cerami, A. (1992). Metabolism and functions of trypanothione in the Kinetoplastida. Annu. Rev. Microbiol. 46:695–729.
8. Krauth-Siegel, R. L., Enders, B., Henderson, G. B., Fairlamb, A. H., and Schirmer, R. H. (1987). Trypanothione reductase from *Trypanosome cruzi*: purification and characterization of the crystalline enzyme. Eur. J. Biochem. 164:123–128.
9. Taylor, M. C., Kelly, J. M., Chapman, C. J., Fairlamb, A. H., and Miles, M. A. (1994). The structure, organization, and expression of the *Leishmania donovani* gene encoding trypanothione reductase. Mol. Biochem. Parasitol. 64:293–301.
10. Papadopoulou, B., Roy, G. and Ouellette, M. (1994). Autonomous replication of bacterial DNA plasmid oligomers in Leishmania. Mol. Biochem. Parasitol. 65:39–49.
11. Cruz, A., Titus, R., and Beverley, S. M. (1993). Plasticity in chromosome number and testing of essential genes in Leishmania by targeting. Proc. Natl. Acad. Sci. USA 90:1599–1603.
12. Charest, H. and Matlashewski, G. (1994). Developmental gene expression in *Leishmania donovani*: differential cloning and analysis of an amastigote stage-specific gene. Mol. Cell. Biol. 14:2975–2984.
13. Brun and Schönenberger (1979) Acta Trop. 36:289.
14. Papadopoulou, B., Roy, G., and Ouellette, M. (1992) A novel antifolate resistance gene on the amplified H circle of Leishmania. EMBO J. 11:3601–3608.
15. Olivier, M., Baimbridge, K. G. and Rainer, N. E. (1992) Stimulus-response coupling in monocytes infected with Leishmania. Attenuation of calcium transients is related to defective agonist-induced accumulation of inositol phosphates. J. Immunol. 148:1188–1196.
16. Taylor, M. C., Kelly, J. M., Chapman, C. J. Fairlamb, A. H. and Miles, M. A. (1994). The structure, organization and expression of the *Leishmania donovani* gene encoding trypanothione reductase. Mol. Biochem. Parasitol. 64:293–301.
17. Ryan, K. A., Dasgupta, S., and Beverley, S. M. (1993) Gene, 131:145
18. Bernards, A., van der Ploeg, L. H. T., Frasch, A. C. C., Borst, P., Boothroyd, J. C., Coleman., S., and Cross, G. A. M. (1981). Activation of trypanosome surface glycoprotein genes involves a duplication-transposition leading to an altered 3' end. Cell 27:497–505.
19. Van der Ploeg L. H. T., Schwartz, D. C., Cantor, C. R., and Borst, P. (1984). Antigenic variation in *Trypanosoma brucei* analysed by electrophoretic separation of chromosome-sized DNA molecules. Cell 37:77–84.
20. Thomashow, L. S., Milhausen, M., Rutter, W. J., and Agabian, N. (1983) Cell 32:35–43.
21. White, T. C., Fase-Fowler, F., van Luenen, H., Calafat, J., and Borst, P. (1988). The H circles of *Leishmania tarentolae* are a unique amplifiable system of oligomeric DNAs associated with drug resistance. J. Biol. Chem. 263: 16977–16983.
22. Thierry, A., Perrin, A., Boyer, J., Fairhead, C. and Dujou, B. (1991), Cleavage of yeast and bacteriophage T7 genomes at a single site using the rare cutter endonuclease I-SceI. Nucleic Acids Res. 19: 189–190.

What we claimed is:

1. A method of generating an immune response in a host comprising administering thereto an immunoeffective amount of an immunogenic composition comprising an attenuated strain of Leishmania wherein both wild-type copies of the gene encoding trypanothione reductase of the strain have been functionally disabled by mutagenesis thereof to provide a mutated strain having a reduced ability to infect or survive within macrophages in comparison to the native strain and a third copy of said gene encoding trypanothione reductase is present in the chromosome of the strain.

2. The method of claim 1 wherein the virulent strain is selected from the group consisting of *Leishmania donovani, Leishmania braziliensis, Leishmania tarentolae, Leishmania major, Leishmania mexicana, Leishmania tropica* and *Leishmania aethiopica*.

* * * * *

UNITED STATES PATENT AND TRADEMARK OFFICE
CERTIFICATE OF CORRECTION

PATENT NO.     : 6,403,081 B1                                         Page 1 of 1
DATED          : June 11, 2002
INVENTOR(S)    : Barbara Papadopoulou et al.

It is certified that error appears in the above-identified patent and that said Letters Patent is hereby corrected as shown below:

<u>Title page,</u>
Item [73], Assignee should read -- Universite Laval --.

Signed and Sealed this

Twenty-fourth Day of June, 2003

JAMES E. ROGAN
*Director of the United States Patent and Trademark Office*